United States Patent
Demattos et al.

(10) Patent No.: US 11,078,261 B2
(45) Date of Patent: Aug. 3, 2021

(54) ANTI-N3PGLU AMYLOID BETA PEPTIDE ANTIBODIES AND USES THEREOF

(71) Applicant: Eli Lilly and Company, Indianapolis, IN (US)

(72) Inventors: Ronald Bradley Demattos, Zionsville, IN (US); Jirong Lu, Carmel, IN (US); Ying Tang, San Diego, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/843,503

(22) Filed: Apr. 8, 2020

(65) Prior Publication Data

US 2020/0262902 A1    Aug. 20, 2020

Related U.S. Application Data

(62) Division of application No. 15/953,716, filed on Apr. 16, 2018, now Pat. No. 10,647,759.

(60) Provisional application No. 62/487,550, filed on Apr. 20, 2017.

(51) Int. Cl.
*C07K 16/18* (2006.01)
*A61P 25/28* (2006.01)
*A61K 39/00* (2006.01)

(52) U.S. Cl.
CPC ............ *C07K 16/18* (2013.01); *A61P 25/28* (2018.01); *A61K 2039/505* (2013.01); *C07K 2317/56* (2013.01); *C07K 2317/565* (2013.01); *C07K 2317/90* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,122,374 B1 | 10/2006 | Saido | |
| 8,679,498 B2 | 3/2014 | Lu | |
| 2007/0031416 A1 | 2/2007 | Asami | |
| 2008/0299111 A1 | 12/2008 | Sergeant | |
| 2010/0021478 A1 | 1/2010 | Demuth | |
| 2016/0297885 A1* | 10/2016 | Kuo | C07K 16/2803 |

FOREIGN PATENT DOCUMENTS

| | | |
|---|---|---|
| WO | 2004013172 A2 | 2/2004 |
| WO | 2006036291 A2 | 4/2006 |
| WO | 2008011348 A2 | 1/2008 |
| WO | 2009149487 A2 | 12/2009 |
| WO | 2010004434 A2 | 1/2010 |
| WO | 2010009987 A2 | 1/2010 |
| WO | 2011151076 A2 | 12/2011 |
| WO | 2012021469 A1 | 2/2012 |
| WO | 2012021475 A2 | 2/2012 |
| WO | 2015175769 A1 | 11/2015 |
| WO | 2016043997 A1 | 3/2016 |
| WO | 2017123517 A1 | 7/2017 |
| WO | 2018005282 A1 | 1/2018 |

OTHER PUBLICATIONS

Oliver Wirths, et al., "Pyroglutamate Abeta pathology in APP/PS1K1 mice, sporadic and familial Alzheimer's disease cases", Journal of Neural Transmission, (2009), vol. 117(1), pp. 85-96.
Donna Wilcock, et al., Passive immunotherapy against Abeta in aged APP-transgenic mice reverses cognitive deficits and depletes parenchymal amyloid deposits in spite of increased vascular amyloid and microhemorrhage:, Journal of Neuroinflammation, (2004), vol. 1(1), p. 24.
Oliver Wirths, et al., "Identification of low molecular weight pyroglutamate Abeta oligomers in Alzheimer disease: a novel for therapy and diagnosis", Journal of Biological Chemistry, (2010), vol. 285(53), pp. 41517-41524.
David Brody, et al., "Active and passive immunotherapy for neurodegenerative disorders", Annual Review of Neuroscience, (2008), vol. 31, pp. 175-193.
Frederique Bard, et al., "Epitope and isotype specificities of antibodies to [beta]-amyloid peptide for protection against Alzheimer's disease-like neuropathy", Proc Natl Acad Science, (2003), vol. 100(4), pp. 2023-2028.
F. Luo, et al., "P2-304: MRI detection and time course of cerebral microhemorrhages during Abeta antibody treatment in living APP transgenic mice", Alzheimer's & Dementia: The Journal of the Alzheimer's Association, (2008), vol. 4(4), p. T461.
Margaret M. Racke, et al., "Exacerbation of cerebral amyloid angiopathy-associated microhemorrhage in amyloid precursor protein transgenic mice by immunotherapy is dependent on antibody recognition of deposited forms of amyloid beta", The Journal of Neuroscience: The Office Journal of the Society for Neuroscience, (2005), vol. 25(3), pp. 629-636.
T.A. Bayer, et al., "Intraneuronal Abeta as a trigger for neuron loss: Can this be translated into human pathology?" , Biochemical Society Transactions, (2011), vol. 39(4), pp. 857-861.
Desikan et al., MRI measures of temporoparietal regions show differential rates of atrophy during prodromal AD. Neurology, 2008;71:819-825.
Fennema-Notestine et al., Structural MRI Biomarkers for Preclinical and Mild Alzheimer's Disease, Human Brain Mapp. Oct. 2009; 30(10): 3238-3253.
Schroeter et al., Immunotiierapy Reduces Vascular Amyloid-beta in PDAPP Mice. The Journal of Neuroscience, Jul. 2, 2008 0 28(27):6787-6793.
DeMattos et al., A Plaque-Specific Antibody Clears Existing beta-amyloid Plaques in Alzheimer's Disease Mice. Neuron 76, 908-920, Dec. 6, 2012, 908-920.

(Continued)

*Primary Examiner* — John D Ulm
(74) *Attorney, Agent, or Firm* — Neelaabh Shankar

(57) ABSTRACT

Antibodies to human N3pGlu Aβ, compositions comprising such N3pGlu Aβ antibodies, and methods of using such N3pGlu Aβ antibodies for the treatment of a disease characterized by deposition of Aβ including clinical or pre-clinical Alzheimer's disease, Down's syndrome, and clinical or pre-clinical cerebral amyloid angiopathy.

9 Claims, No Drawings

Specification includes a Sequence Listing.

(56) References Cited

OTHER PUBLICATIONS

Moro et al. Acta Neuropathologica Communications (2018) 6:3.
Anke Piechotta et al., Structural and functional analyses of pyroglutamateamyloid-amyloid-β-specific antibodies as a basis for Alzheimer immunotherapy J. Biol. Chem. (2017) 292(30) 12713-12724.
Jeffrey L Cummins, et al: "Alzheimer's disease drug-development pipeline: few candidates, frequent failures", Alzheimers Res Ther, BioMed Central LTD, London UK, vol. 6, No. 4, Jul. 3, 2014.
Sage C Arbor, et al "Amyloid-beta Alzheimer targets—protein processing, lipid rafts, and amyloid-beta pores", The Yale Journal or biology and medicine, Mar. 1, 2016, p. 5.
Kitazawa et al., Transgenic Mouse Models of Alzheimer Disease: Developing a Better Model as a Tool for Therapeutic Interventions, 2012, Curr Pharm Des.18(8): 1131-1147. (Year: 2012).

* cited by examiner

ANTI-N3PGLU AMYLOID BETA PEPTIDE ANTIBODIES AND USES THEREOF

The present invention relates to antibodies that bind human N3pGlu Amyloid Beta peptide and their use in treating diseases related to Amyloid Beta (herein referred to as Aβ or Abeta) peptide.

The cleavage of the amyloid precursor protein results in Aβ peptides ranging in size from 38 to 43 amino acids. Conversion of Aβ from soluble to insoluble forms having high β-sheet content and the deposition of these insoluble forms as neuritic and cerebrovascular plaques in the brain has been associated with a number of conditions and diseases, including Alzheimer's disease (AD), Down's syndrome, and cerebral amyloid angiopathy (CAA).

The deposits found in plaques are comprised of a heterogeneous mixture of Aβ peptides. N3pGlu Aβ, also referred to as N3pE, pE3-X, or $A\beta_{p3-x}$, is an N-terminal truncated form of Aβ peptide and is primarily found in plaque. N3pGlu Aβ lacks the first two amino acid residues at the N-terminus of human Aβ and has a pyroglutamate which was derived from the glutamic acid at the third amino acid position. Although N3pGlu Aβ peptide is a minor component of the deposited Aβ in the brain, studies have demonstrated that N3pGlu Aβ peptide has aggressive aggregation properties and accumulates early in the deposition cascade.

Antibodies to N3pGlu Aβ are known in the art. For example, U.S. Pat. No. 8,679,498 discloses human N3pGlu Aβ antibodies (e.g. B12L; also known as LY3002813) and methods of treating diseases, such as Alzheimer's disease, with said antibodies. A clinical trial has demonstrated concerns with anti-drug antibodies against an anti-N3pGlu Aβ antibody (LY3002813). Anti-drug antibodies were present in the plasma of almost everyone treated in this trial, and an associated problem with the immune reaction was a shortened half-life of LY3002813. Therefore, there still remains a need for alternative anti-N3pGlu Aβ antibodies.

The antibodies of the present invention seek to provide anti-N3pGlu Aβ antibodies that bind N3pGlu Aβ, lower plaque ($A\beta_{1-42}$) in vivo, but which also demonstrate reduced immunogenicity. Such anti-N3pGlu Aβ antibodies may also demonstrate reduced non-specific binding to plasma proteins. In addition, such anti-N3pGlu Aβ antibodies may also provide a reduced predicted T-Dependent Ab Response. Such anti-N3pGlu Aβ antibodies may also provide increased antibody half-life and an improved safety profile for a potential human therapeutic with pharmacokinetics for a better dosing schedule. The antibodies within the scope of the present invention seek to possess at least one of these desirable characteristics.

The present invention provides an antibody that binds human N3pGlu Aβ, comprising an LCVR and an HCVR, wherein said LCVR comprises LCDR1, LCDR2, and LCDR3, and wherein said HCVR comprises HCDR1, HCDR2, and HCDR3, and wherein the amino acid sequences are SEQ ID NO:4 or 5 for LCDR1, SEQ ID NO:6 or 7 for LCDR2, SEQ ID NO:8 for LCDR3, SEQ ID NO:1 for HCDR1, SEQ ID NO:2 for HCDR2, and SEQ ID NO:3 for HCDR3. In a particular embodiment, the anti-N3pGlu Aβ antibody comprises the amino sequences of SEQ ID NO:4 for LCDR1, SEQ ID NO:6 for LCDR2, SEQ ID NO:8 for LCDR3, SEQ ID NO: 1 for HCDR1, SEQ ID NO: 2 for HCDR2, and SEQ ID NO:3 for HCDR3. In another particular embodiment, the anti-N3pGlu Aβ antibody comprises the amino sequences of SEQ ID NO:5 for LCDR1, SEQ ID NO:7 for LCDR2, SEQ ID NO:8 for LCDR3, SEQ ID NO: 1 for HCDR1, SEQ ID NO:2 for HCDR2, and SEQ ID NO:3 for HCDR3.

The present invention also provides an antibody that binds human N3pGlu Aβ, wherein said antibody comprises a light chain variable region (LCVR) having the amino acid sequence of SEQ ID NO: 10 or SEQ ID NO: 11, and a heavy chain variable region (HCVR) having the amino acid sequence of SEQ ID NO: 9. In a particular embodiment, the present invention provides an antibody that binds human N3pGlu Aβ, wherein said antibody comprises a light chain variable region (LCVR) having the amino acid sequence of SEQ ID NO: 10, and a heavy chain variable region (HCVR) having the amino acid sequence of SEQ ID NO: 9. In another particular embodiment, the present invention provides an antibody that binds human N3pGlu Aβ, wherein said antibody comprises a light chain variable region (LCVR) having the amino acid sequence of SEQ ID NO: 11, and a heavy chain variable region (HCVR) having the amino acid sequence of SEQ ID NO: 9.

In an embodiment, the present invention provides an antibody that binds human N3pGlu Aβ, comprising a light chain (LC) and a heavy chain (HC), wherein the amino acid sequence of the LC is SEQ ID NO: 13 or 14, and the amino acid sequence of the HC is SEQ ID NO: 12. In a more particular embodiment, the present invention provides an antibody that binds human N3pGlu Aβ, comprising a light chain (LC) and a heavy chain (HC), wherein the amino acid sequence of the LC is SEQ ID NO: 13, and the amino acid sequence of the HC is SEQ ID NO: 12. In another particular embodiment, the present invention provides an antibody that binds human N3pGlu Aβ, comprising a light chain (LC) and a heavy chain (HC), wherein the amino acid sequence of the LC is SEQ ID NO: 14, and the amino acid sequence of the HC is SEQ ID NO: 12. In a further embodiment, the present invention provides an antibody comprising two LC and two HC, wherein the amino acid sequence of each LC is SEQ ID NO: 13 or 14, and the amino acid sequence of each HC is SEQ ID NO: 12. In a more particular embodiment, the present invention provides an antibody comprising two LC and two HC, wherein the amino acid sequence of each LC is SEQ ID NO: 13, and the amino acid sequence of each HC is SEQ ID NO: 12. In a more particular embodiment, the present invention provides an antibody comprising two LC and two HC, wherein the amino acid sequence of each LC is SEQ ID NO: 14, and the amino acid sequence of each HC is SEQ ID NO: 12.

The present invention further provides pharmaceutical compositions comprising an antibody of the present invention and one or more pharmaceutically acceptable carriers, diluents or excipients. Further, the present invention provides a method of treating a disease characterized by deposition of Aβ, comprising administering to a patient in need thereof a pharmaceutical composition comprising an antibody of the present invention. In another embodiment, the present invention provides a method of treating a disease characterized by deposition of Aβ, comprising administering an effective amount of an antibody of the present invention. Particularly, the present invention provides a method of treating or preventing a condition selected from clinical or pre-clinical Alzheimer's disease, Down's syndrome, and clinical or pre-clinical CAA comprising administering to said patient an effective amount of an antibody of the present invention. In another embodiment, the present invention provides a method of treating or preventing clinical or pre-clinical Alzheimer's disease, Down's syndrome, and clinical or pre-clinical CAA comprising administering to a patient in need thereof an effective amount of a pharmaceutical composition comprising an antibody of the present invention. In another embodiment, the present invention provides a method of treating or preventing a condition selected from prodromal AD (sometimes also referred to as Aβ-related mild cognitive impairment, or MCI), mild AD, moderate AD, and severe AD, comprising administering to a patient in need thereof an effective amount of an antibody of the present invention. In another embodiment, the present invention provides a method of treating or preventing a condition selected from prodromal AD, mild AD, moderate AD, and severe AD, comprising administering to a patient in need thereof a pharmaceutical composition comprising an antibody of the present invention.

In another embodiment the present invention provides a method of slowing cognitive decline in a patient diagnosed with pre-clinical Alzheimer's disease, clinical Alzheimer's disease, Down's syndrome, or clinical or pre-clinical cerebral amyloid angiopathy, comprising administering a pharmaceutical composition comprising an antibody of the present invention. More particularly, the present invention further provides a method of slowing cognitive decline in a patient diagnosed with a condition selected from prodromal AD, mild AD, moderate AD and severe AD, comprising administering a pharmaceutical composition comprising an antibody of the present invention. In another such embodiment the present invention provides a method of slowing cognitive decline in a patient diagnosed with pre-clinical Alzheimer's disease, clinical Alzheimer's disease, Down's syndrome, or clinical or pre-clinical cerebral amyloid angiopathy, comprising administering an effective amount of an antibody of the present invention. More particularly, the present invention further provides a method of slowing cognitive decline in a patient diagnosed with a condition selected from prodromal AD, mild AD, moderate AD and severe AD, comprising administering an effective amount of an antibody of the present invention.

In another embodiment the present invention provides a method of slowing functional decline in a patient diagnosed with pre-clinical Alzheimer's disease or clinical Alzheimer's disease, comprising administering a pharmaceutical composition comprising an antibody of the present invention. More particularly, the present invention provides a method of slowing functional decline in a patient diagnosed with a condition selected from prodromal AD, mild AD, moderate AD and severe AD, comprising administering a pharmaceutical composition comprising an antibody of the present invention. In another such embodiment the present invention provides a method of slowing functional decline in a patient diagnosed with pre-clinical Alzheimer's disease or clinical Alzheimer's disease, comprising administering an effective amount of an antibody of the present invention. More particularly, the present invention provides a method of slowing functional decline in a patient diagnosed with a condition selected from prodromal AD, mild AD, moderate AD and severe AD, comprising administering an effective amount of an antibody of the present invention.

In another embodiment the present invention provides a method of reducing brain Aβ amyloid plaque load in a patient diagnosed with pre-clinical or clinical Alzheimer's disease, comprising administering a pharmaceutical composition comprising an antibody of the present invention. More particularly, the present invention provides a method of reducing brain Aβ amyloid plaque load in a patient diagnosed with a condition selected from prodromal AD, mild AD, moderate AD or severe AD, comprising administering a pharmaceutical composition comprising an antibody of the present invention.

In another embodiment the present invention provides a method of preventing memory loss or cognitive decline in an asymptomatic patient comprising administering to the patient a pharmaceutical composition comprising an antibody of the present invention. In a preferred embodiment, the patient has low levels of Aβ1-42 in the cerebrospinal fluid (CSF) or Aβ plaques in the brain.

In another embodiment the present invention provides a method of treating asymptomatic patients known to have an Alzheimer's disease-causing genetic mutation, comprising administering to the said patient a pharmaceutical composition comprising an antibody of the present invention. In a particular embodiment, the present invention provides a method of treating asymptomatic patients known to have a PSEN1 E280A Alzheimer's disease-causing genetic mutation (Paisa mutation), comprising administering to the said patient a pharmaceutical composition comprising an antibody of the present invention. In another particular embodiment, the present invention provides a method of treating asymptomatic patients with a genetic mutation, such as a mutation in the APP, PSEN1, or PSEN2 gene, that causes autosomal-dominant Alzheimer's disease, comprising administering to the said patient a pharmaceutical composition comprising an antibody of the present invention.

In another embodiment the present invention provides a method of preventing memory loss or cognitive decline in asymptomatic patients known to have an Alzheimer's disease-causing genetic mutation, comprising administering to the said patient a pharmaceutical composition comprising an antibody of the present invention. In a particular embodiment, the present invention provides a method of preventing memory loss or cognitive decline in asymptomatic patients known to have a PSEN1 E280A Alzheimer's disease-causing genetic mutation (Paisa mutation), comprising administering to the said patient a pharmaceutical composition comprising an antibody of the present invention. In another particular embodiment, the present invention provides a method of preventing memory loss or cognitive decline in asymptomatic patients with a genetic mutation that causes autosomal-dominant Alzheimer's disease, comprising administering to the said patient a pharmaceutical composition comprising an antibody of the present invention.

In another embodiment the present invention provides a method of slowing cognitive decline in an asymptomatic patient known to have an Alzheimer's disease-causing genetic mutation, comprising administering to the said patient a pharmaceutical composition comprising an antibody of the present invention. In a particular embodiment, the present invention provides a method of slowing cognitive decline in asymptomatic patients known to have a PSEN1 E280A Alzheimer's disease-causing genetic mutation (Paisa mutation), comprising administering to the said patient a pharmaceutical composition comprising an antibody of the present invention. In another particular embodiment, the present invention provides a method of slowing cognitive decline in asymptomatic patients with a genetic mutation that causes autosomal-dominant Alzheimer's disease, comprising administering to the said patient a pharmaceutical composition comprising an antibody of the present invention.

The present invention also provides an antibody of the present invention for use in therapy. In an embodiment, the present invention provides an antibody of the present invention for use in the treatment of a disease characterized by deposition of Aβ. In another embodiment, the present invention provides an antibody of the present invention for use in treatment of clinical or pre-clinical Alzheimer's disease, Down's syndrome, or clinical or pre-clinical cerebral amyloid angiopathy. In another embodiment, the present invention provides an antibody of the present invention for use in treatment of a condition selected from prodromal AD, mild AD, moderate AD and severe AD. In another embodiment, the present invention provides an antibody of the present invention for use in slowing cognitive decline in a patient diagnosed with clinical or pre-clinical Alzheimer's disease, Down's syndrome, or clinical or pre-clinical cerebral amyloid angiopathy. In another embodiment, the present invention provides an antibody of the present invention for use in slowing cognitive decline in a patient diagnosed with prodromal AD, mild AD, moderate AD, or severe AD.

The present invention also provides an antibody of the present invention for use in reducing brain Aβ amyloid plaque load. In another embodiment, the present invention provides an antibody of the present invention for use in treating a condition characterized by deposition of Aβ in a patient having the PSEN1 E280A genetic mutation. In another embodiment, the present invention provides an antibody of the present invention for use in treating memory loss or cognitive decline in a patient having the PSEN1 E280A genetic mutation. In another embodiment, the present invention provides an antibody of the present invention for use in preventing memory loss or cognitive decline in a patient having the PSEN1 E280A genetic mutation.

The present invention also provides an antibody of the present invention for use in the prevention of a condition selected from clinical or pre-clinical AD, Down's syndrome, and clinical or pre-clinical CAA. In another embodiment, the present invention provides an antibody of the present invention for use in the prevention of a condition selected from prodromal AD, mild AD, moderate AD, and severe AD.

Further, the present invention provides a pharmaceutical composition comprising an antibody of the present invention for use in therapy. In an embodiment, the present invention provides a pharmaceutical composition comprising an antibody for use in the treatment of a disease characterized by deposition of Aβ.

The present invention also provides the use of an antibody of the present invention in the manufacture of a medicament for the treatment of a disease characterized by deposition of Aβ. In an embodiment, the present invention provides the use of an antibody of the present invention in the manufacture of a medicament for the treatment of clinical or pre-clinical Alzheimer's disease, Down's syndrome, and clinical or pre-clinical cerebral amyloid angiopathy. In an embodiment, the present invention provides the use of an antibody of the present invention in the manufacture of a medicament for the treatment of prodromal AD, mild AD, moderate AD or severe AD. In another embodiment, the present invention provides the use of an antibody of the present invention in the manufacture of a medicament for slowing cognitive decline in a patient diagnosed with a condition selected from clinical or pre-clinical Alzheimer's disease, Down's syndrome, and clinical or pre-clinical cerebral amyloid angiopathy. In another embodiment, the present invention provides the use of an antibody of the present invention in the manufacture of a medicament for slowing cognitive decline in a patient diagnosed with a condition selected from prodromal AD, mild AD, moderate AD and severe AD.

The present invention also provides the use of an antibody of the present invention in the manufacture of a medicament for reducing brain Aβ amyloid plaque load. In another embodiment, the present invention provides the use of an antibody of the present invention in the manufacture of a medicament for treating a condition characterized by deposition of Aβ in a patient having the PSEN1 E280A genetic mutation. In another embodiment, the present invention provides the use of an antibody of the present invention in the manufacture of a medicament for treating memory loss or cognitive decline in a patient having the PSEN1 E280A genetic mutation. In another embodiment, the present invention provides the use of an antibody of the present invention in the manufacture of a medicament for preventing memory loss or cognitive decline in a patient. In a preferred embodiment, the patient has the PSEN1 E280A genetic mutation. In another embodiment, the present invention provides the use of an antibody of the present invention in the manufacture of a medicament for preventing a condition selected from clinical or pre-clinical AD, Down's syndrome, and clinical or pre-clinical CAA. In another embodiment, the present invention provides the use of an antibody of the present invention in the manufacture of a medicament for preventing a condition selected from prodromal AD, mild AD, moderate AD, and severe AD.

In an embodiment, the present invention provides a DNA molecule comprising a polynucleotide sequence encoding a polypeptide having the amino acid sequence of SEQ ID NO: 12. In an embodiment, the present invention provides a DNA molecule comprising a polynucleotide sequence encoding a polypeptide having the amino acid sequence of SEQ ID NO: 13. In an embodiment, the present invention provides a DNA molecule comprising a polynucleotide sequence encoding a polypeptide having the amino acid sequence of SEQ ID NO: 14. In a further embodiment, the present invention provides a DNA molecule comprising a polynucleotide sequence encoding a polypeptide having the amino acid sequence of SEQ ID NO: 12, and comprising a polynucleotide sequence encoding a polypeptide having the amino acid sequence of SEQ ID NO: 13. In another embodiment, the present invention provides a DNA molecule comprising a polynucleotide sequence encoding a polypeptide having the amino acid sequence of SEQ ID NO: 12, and comprising a polynucleotide sequence encoding a polypeptide having the amino acid sequence of SEQ ID NO: 14. In another embodiment, the present invention provides a DNA molecule comprising a polynucleotide sequence encoding a polypeptide having the amino acid sequence of SEQ ID NO: 12, and a DNA molecule comprising a polynucleotide sequence encoding a polypeptide having the amino acid sequence of SEQ ID NO: 13. In another embodiment, the present invention provides a DNA molecule comprising a polynucleotide sequence encoding a polypeptide having the amino acid sequence of SEQ ID NO: 12, and a DNA molecule comprising a polynucleotide sequence encoding a polypeptide having the amino acid sequence of SEQ ID NO: 14. In a particular embodiment the polynucleotide sequence encoding a polypeptide having the amino acid sequence of SEQ ID NO: 12 is SEQ ID NO: 15 and the polynucleotide sequence encoding a polypeptide having the amino acid sequence of SEQ ID NO: 13 is SEQ ID NO: 16. In a particular embodiment the polynucleotide sequence encoding a polypeptide having the amino acid sequence of SEQ ID NO: 12 is SEQ ID NO: 15, the polynucleotide sequence encoding a polypeptide having the amino acid sequence of SEQ ID NO: 14 is SEQ ID NO: 17, and the polynucleotide sequence encoding a polypeptide having the amino acid sequence of SEQ ID NO: 13 is SEQ ID NO: 16.

Further, the present invention provides a mammalian cell comprising a DNA molecule comprising a polynucleotide sequence encoding a polypeptide having the amino acid sequence of SEQ ID NO: 12 and a DNA molecule comprising a polynucleotide sequence encoding a polypeptide having the amino acid sequence of SEQ ID NO: 13 or 14. Preferably the mammalian cell comprises a DNA molecule comprising a polynucleotide sequence encoding a polypeptide having the amino acid sequence of SEQ ID NO: 12 and a polypeptide having the amino acid sequence SEQ ID NO: 13. In another embodiment, the mammalian cell comprises a DNA molecule comprising a polynucleotide sequence encoding a polypeptide having the amino acid sequence of SEQ ID NO: 12 and a polypeptide having the amino acid sequence of SEQ ID NO: 14. In an embodiment the mammalian cell line is a Chinese Hamster Ovary (CHO) or Hamster embryonic kidney (HEK) cell line.

The present invention also provides a mammalian cell comprising a DNA molecule comprising a polynucleotide sequence encoding a polypeptide having the amino acid sequence of SEQ ID NO:12 and/or a DNA molecule comprising a polynucleotide sequence encoding a polypeptide having the amino acid sequence of SEQ ID NO: 13, wherein the cell is capable of expressing an antibody comprising a HC having the amino acid sequence of SEQ ID NO:12 and a LC having the amino acid sequence of SEQ ID NO: 13. Preferably the mammalian cell comprises a DNA molecule comprising a polynucleotide sequence encoding a polypeptide having the amino acid sequence of SEQ ID NO:12 and a polypeptide having the amino acid sequence SEQ ID NO: 13. The present invention also provides a mammalian cell comprising a DNA molecule comprising a polynucleotide sequence encoding a polypeptide having the amino acid sequence of SEQ ID NO:12 and/or a DNA molecule comprising a polynucleotide sequence encoding a polypeptide having the amino acid sequence of SEQ ID NO: 13, wherein the cell is capable of expressing an antibody comprising a HC having the amino acid sequence of SEQ ID NO:12 and a LC having the amino acid sequence of SEQ ID NO: 13. Preferably the mammalian cell comprises a DNA molecule comprising a polynucleotide sequence encoding a polypeptide having the amino acid sequence of SEQ ID NO:12 and a polypeptide having the amino acid sequence SEQ ID NO: 13. In an embodiment the mammalian cell line is a CHO or HEK cell line.

In another embodiment, the present invention provides a process for producing an antibody comprising a LCVR having an amino acid sequence of SEQ ID NO: 10 and a HCVR having an amino acid sequence of SEQ ID NO:9, wherein the process comprises cultivating a mammalian cell comprising a DNA encoding an LCVR having an amino acid sequence of SEQ ID NO: 10 and/or a DNA encoding an HCVR having an amino acid sequence of SEQ ID NO:9 under conditions such that the antibody is expressed, and recovering the expressed antibody. The invention includes an antibody obtainable by the process of the invention as described immediately above. The present invention also provides a process for producing an antibody comprising a LCVR having an amino acid sequence of SEQ ID NO: 11 and a HCVR having an amino acid sequence of SEQ ID NO:9, wherein the process comprises cultivating a mammalian cell comprising a DNA encoding an LCVR having an amino acid sequence of SEQ ID NO: 11 and/or a HCVR having an amino acid sequence of SEQ ID NO:9 under conditions such that the antibody is expressed, and recovering the expressed antibody. The invention includes an antibody obtainable by the process of the invention as described immediately above.

In another embodiment, the present invention provides a process for producing an antibody comprising a LC having an amino acid sequence of SEQ ID NO: 13 and a HC having an amino acid sequence of SEQ ID NO: 12, wherein the process comprises cultivating a mammalian cell comprising a DNA encoding a LC having an amino acid sequence of SEQ ID NO: 13 and/or a HC having an amino acid sequence of SEQ ID NO: 12 under conditions such that the antibody is expressed, and recovering the expressed antibody. The invention includes an antibody obtainable by the process of the invention as described immediately above. The present invention also provides a process for producing an antibody comprising a LC having an amino acid sequence of SEQ ID NO: 14 and a HC having an amino acid sequence of SEQ ID NO: 12, wherein the process comprises cultivating a mammalian cell comprising a DNA encoding a LC having an amino acid sequence of SEQ ID NO: 14 and/or a HC having an amino acid sequence of SEQ ID NO: 12 under conditions such that the antibody is expressed, and recovering the expressed antibody. The invention includes an antibody obtainable by the process of the invention as described immediately above.

The present invention includes a process for producing an antibody, which antibody comprises two HCs and two LCs, in which the amino sequence of each of the two HCs is SEQ ID NO: 12, and the amino acid sequence of each of the two LCs is SEQ ID NO: 13, and which process comprises: a) cultivating a mammalian cell of the invention, as described above, under conditions such that the antibody is expressed, and b) recovering the expressed antibody. The invention includes an antibody obtainable by the process of the invention as described immediately above. The present invention also includes a process for producing an antibody, which antibody comprises two HCs and two LCs, in which the amino sequence of each of the two HCs is SEQ ID NO: 12 and the amino acid sequence of each of the two LCs is SEQ ID NO: 14, and which process comprises: a) cultivating a mammalian cell of the invention, as described above, under conditions such that the antibody is expressed, and b) recovering the expressed antibody. The invention includes an antibody obtainable by the process of the invention as described immediately above.

The antibodies of the present invention bind to N3pGlu Aβ. The sequence of N3pGlu Aβ is the amino acid sequence of SEQ ID NO: 22, and carboxyl terminal variants thereof. Examples of a carboxyl terminal variants of N3pGlu Aβ include $A\beta_{p3-40}$ and $A\beta_{p3-43}$.

As used herein, an "antibody" is an immunoglobulin molecule comprising two heavy chains (HC) and two light chains (LC) interconnected by disulfide bonds. The amino terminal portion of each LC and HC includes a variable region responsible for antigen recognition via the complementarity determining regions (CDRs) contained therein. The CDRs are interspersed with regions that are more conserved, termed framework regions. Assignment of amino acids to CDR domains within the LCVR and HCVR regions of the antibodies of the present invention is based on the well-known Kabat numbering convention (Kabat, et al., Ann. NY Acad. Sci. 190:382-93 (1971); Kabat et al., Sequences of Proteins of Immunological Interest, Fifth Edition, U.S. Department of Health and Human Services, NIH Publication No. 91-3242 (1991)), and North numbering convention (North et al., A New Clustering of Antibody CDR Loop Conformations, Journal of Molecular Biology, 406:228-256 (2011)).

The antibodies of the present invention include kappa LC and IgG HC. In a particular embodiment, the antibodies of the present invention are IgG1.

The antibodies of the present invention are monoclonal antibodies ("mAbs"). Monoclonal antibodies can be produced, for example, by hybridoma technologies, recombinant technologies, phage display technologies, synthetic technologies, e.g., CDR-grafting, or combinations of such or other technologies known in the art. In another embodiment of the present invention, the antibody, or the nucleic acid encoding the same, is provided in isolated form. As used herein, the term "isolated" refers to a protein, peptide or nucleic acid that is not found in nature and is free or substantially free from other macromolecular species found in a cellular environment. "Substantially free", as used herein, means the protein, peptide or nucleic acid of interest comprises more than 80% (on a molar basis) of the macromolecular species present, preferably more than 90% and more preferably more than 95%.

Following expression and secretion of the antibody, the medium is clarified to remove cells and the clarified media is purified using any of many commonly-used techniques. The purified antibody may be formulated into pharmaceutical compositions according to well-known methods for formulating proteins and antibodies for parenteral administration, particularly for subcutaneous, intrathecal, or intravenous administration. The antibody may be lyophilized, together with appropriate pharmaceutically-acceptable excipients, and then later reconstituted with a water-based diluent prior to use. Alternatively, the antibody may be formulated in an aqueous solution and stored for up to 1-3 years prior to use. In either case, the stored form and the injected form of the pharmaceutical compositions of the antibody will contain a pharmaceutically-acceptable excipient or excipients, which are ingredients other than the antibody. Whether an ingredient is pharmaceutically-acceptable depends on its effect on the safety and effectiveness or on the purity, and potency of the pharmaceutical composition. If an ingredient is judged to have a sufficiently unfavorable effect on safety or effectiveness (or on purity or potency) to warrant it not being used in a composition for administration to humans, then it is not pharmaceutically-acceptable to be used in a pharmaceutical composition of the antibody.

A pharmaceutical composition comprising an antibody of the present invention can be administered to a patient at risk for, or exhibiting, diseases or disorders as described herein by parental routes (e.g., subcutaneous, intravenous, intraperitoneal, intramuscular). Subcutaneous and intravenous routes are preferred. A pharmaceutical composition of the present invention contains an "effective" amount of an antibody of the present invention. An effective amount refers to an amount necessary (at dosages and for periods of time and for the means of administration) to achieve the desired therapeutic result. An effective amount of the antibody may vary according to factors such as the disease state, age, sex, and weight of the individual, and the ability of the antibody to elicit a desired response in the individual. An effective amount can be readily determined by the attending diagnostician or health care professional, as one skilled in the art, by using known techniques and by observing results. Frequency of dosing is dependent on actual pharmacokinetics and pharmacodynamics in humans. Duration of treatment will vary depending on many factors and it will be determined by the patient's diagnostician or treating health care provider, based on experience and skill in the art. Frequency and duration of treatment may vary by indication. The terms "treatment," "treating" or "to treat" and the like include restraining, slowing or stopping the progression or severity of an existing symptom, condition, disease, or disorder in a patient. The term "patient" refers to a human. The terms "prevent" and "preventing" means prophylactic administration of an antibody of the present invention to an asymptomatic patient in order to keep the patient from having symptoms or clinical features of neurodegenerative diseases such as AD.

The term "condition characterized by deposition of Aβ," is a disease that is pathologically characterized by Aβ deposits in the brain or in brain vasculature. This includes diseases such as Alzheimer's disease, Down's syndrome, and cerebral amyloid angiopathy. A clinical diagnosis, staging or progression of Alzheimer's disease can be readily determined by the attending diagnostician or health care professional, as one skilled in the art, by using known techniques and by observing results. This generally includes some form of brain plaque imagining, mental or cognitive assessment (e.g. Clinical Dementia Rating—summary of boxes (CDR-SB), Mini-Mental State Exam (MMSE) or Alzheimer's Disease Assessment Scale-Cognitive (ADAS-Cog)) or functional assessment (e.g. Alzheimer's Disease Cooperative Study-Activities of Daily Living (ADCS-ADL). "Clinical Alzheimer's disease" as used herein is a diagnosed stage of Alzheimer's disease. It includes conditions diagnosed as prodromal Alzheimer's disease, mild Alzheimer's disease, moderate Alzheimer's disease and severe Alzheimer's disease. The term "pre-clinical Alzheimer's disease" is a stage that precedes clinical Alzheimer's disease, where measurable changes in biomarkers (such as CSF Aβ42 levels or deposited brain plaque load by amyloid PET) indicate the earliest signs of a patient with Alzheimer's pathology, progressing to clinical Alzheimer's disease. This is usually before symptoms such as memory loss and confusion are noticeable.

The following Examples and assays demonstrate that the antibodies of the present invention are useful for treating a disease characterized by deposition of Aβ, such as of Alzheimer's disease, Down's syndrome, and CAA. It should be understood however, that the following Examples are set forth by way of illustration and not limitation, and that various modifications may be made by one of ordinary skill in the art.

EXAMPLES

Expression and Purification of Engineered N3pGlu Aβ Antibodies

N3pGlu Aβ antibodies of the present invention can be expressed and purified essentially as follows. A glutamine synthetase (GS) expression vector containing the DNA sequence encoding the LC amino acid sequence of SEQ ID NO: 13 or 14, and the DNA sequence encoding the HC amino acid sequence of SEQ ID NO: 12 is used to transfect a Chinese hamster ovary cell line (CHO) by electroporation. The expression vector encodes an SV Early (Simian Virus 40E) promoter and the gene for GS. Post-transfection, cells undergo bulk selection with 0-50 μM L-methionine sulfoximine (MSX). Selected bulk cells or master wells are then scaled up in serum-free, suspension cultures to be used for production.

Clarified medium, into which the antibody has been secreted, is applied to a Protein A affinity column that has been equilibrated with a compatible buffer, such as phosphate buffered saline (pH 7.4). The column is washed with 1 M NaCl to remove nonspecific binding components. The bound N3pGlu Aβ antibody is eluted, for example, with sodium citrate at pH (approx.) 3.5 and fractions are neutralized with 1 M Tris buffer. N3pGlu Aβ antibody fractions are detected, such as by SDS-PAGE or analytical size-exclusion, and then are pooled. N3pGlu Aβ antibody of the present invention is concentrated in either PBS buffer at pH 7.4 or 10 mM NaCitrate buffer, 150 mM NaCl at pH around 6. The final material can be sterile filtered using common techniques. The purity of N3pGlu Aβ antibody is greater than 95%. An N3pGlu Aβ antibody of the present invention may be immediately frozen at −70° C. or stored at 4° C. for several months. Amino acid SEQ ID NOs for exemplified antibodies of the present invention are shown below.

TABLE 1

Amino acid sequences of exemplified N3pGlu Aβ antibodies.

Antibody SEQ ID NOs

| Antibody | Light Chain | Heavy Chain | LCVR | HCVR |
|---|---|---|---|---|
| 201c | 13 | 12 | 10 | 9 |
| 201cYD | 14 | 12 | 11 | 9 |

Antibody SEQ ID NOs

| Antibody | LCDR1 | LCDR2 | LCDR3 |
|---|---|---|---|
| 201c | 4 | 6 | 8 |
| 201cYD | 5 | 7 | 8 |

Antibody SEQ ID NOs

| Antibody | HCDR1 | HCDR2 | HCDR3 |
|---|---|---|---|
| 201c and 201cYD | 1 | 2 | 3 |

Binding Kinetics and Avidity

The binding kinetics and avidity of N3pGlu Aβ antibody to pE3-42 Aβ peptide is measured by surface plasmon resonance using Biacore® 3000 (GE Healthcare). The binding avidity is measured by immobilizing about 120 RU pE3-42 Aβ peptide via amine coupling on a Biacore® CMS chip, and flowing N3pGlu Aβ antibody, starting from 500 nM in 2-fold serial dilution down to 15.6 nM. The experiments are carried out at 25° C. in HBS-EP buffer (GE Healthcare BR100669; 10 mM HEPES, 150 mM NaCl, 3 mM EDTA, 0.05% surfactant P20, pH 7.4). For each cycle, 250 µL antibody sample is flowed through flow cell 1 and 2 at 50 µl/min, and then dissociated for 10 minutes. The chip surface is regenerated with 5 µL injection of glycine buffer at pH 1.5 at 10 µL/mL flow rate. The data is fit to a 1:1 Langmiur binding model to derive $k_{on}$, $k_{off}$, and to calculate $K_D$. Following procedures essentially as described above, the following parameters (shown in Table 2) were observed.

TABLE 2

Binding kinetics and avidity.

| Antibody | | Kon (1/Ms) | Koff (1/s) | $K_D(M)$ |
|---|---|---|---|---|
| 201c | Mean | 1.64E+03 | 6.98E−05 | 4.57E−08 |
| | S.D. | 3.88E+02 | 1.36E−05 | 2.06E−08 |
| 201cYD | Mean | 2.41E+03 | 6.39E−05 | 2.67E−08 |
| | S.D. | 2.01E+02 | 2.15E−06 | 2.61E−09 |

These data demonstrate that the antibodies of the present invention bind pE3-42 Aβ.

Ex Vivo Target Engagement

To determine ex vivo target engagement on brain sections from a fixed PDAPP brain, immunohistochemical analysis is performed with exogenously added N3pGlu Aβ antibodies of the present invention or the 201c H3B antibody. The 201c H3B antibody differs by one amino acid from the 201c antibody, and this difference is located in the heavy chain HCDR3 (Tyr at position 10 in 201c HCDR3 is Phe in 201c H3B). The 201c H3B antibody comprises a heavy chain amino acid sequence given by SEQ ID NO: 20 and a light chain amino acid sequence given by SEQ ID NO: 13.

Cryostat serial coronal sections from aged PDAPP mice (26 or 20-month old) are incubated with 5 µg/mL or 20 µg/mL of an exemplified N3pGlu Aβ antibody of the present invention (201c or 201cYD). Secondary HRP reagents specific for human IgG are employed and the deposited plaques are visualized with DAB-Plus (DAKO). Biotinylated murine 3D6 antibody followed by Step-HRP secondary is used as a positive control.

The exemplified N3pGlu Aβ antibodies of the present invention labeled deposited Aβ in these brain sections. However, a higher background staining for the 201c H3B antibody at the exogenous 20 µg/ml concentration was observed. These histological studies demonstrated that the exemplified N3pGlu Aβ antibodies of the present invention engaged deposited Aβ target ex vivo.

Ex Vivo Phagocytosis

An ex vivo phagocytosis assay is performed to investigate whether N3pGlu Aβ antibodies of the present invention can facilitate microglial phagocytosis of plaque. Frozen sections from human Alzheimer's brain (20 µm) are pre-incubated with 10 µg/mL of an exemplified N3pGlu Aβ antibody of the present invention (201c or 201cYD), controls, or the 201c H3B antibody for one hour at 37° C. in 24-well plates. There are four wells per treatment. Primary murine microglia cells ($8 \times 10^5$; C57/BL6) are then added and incubated for 24 hours. Tissue in each well is homogenized in 5.2 M guanidine buffer and the $A\beta_{1-42}$ content is evaluated by ELISA. Since the Aβ content can vary over the span of multiple sections, a sister section control is implemented for every test well and the content of the test well is normalized to that of the sister section.

Compared to the positive control samples, exemplified N3pGlu Aβ antibodies of the present invention (201c and 201cYD) and 201c H3B had significantly reduced $A\beta_{1-42}$. The negative control samples had negligible clearance of deposited $A\beta_{1-42}$. Therefore, ex vivo phagocytosis analyses show that exemplified N3pGlu Aβ antibodies of the present invention can clear plaque ex vivo by phagocytosis.

In Vivo Target Engagement

The ability of N3pGlu Aβ antibodies of the present invention to cross the blood-brain-barrier and bind to deposited plaque in vivo is measured. Aged PDAPP transgenic mice (18.5 to 32 months of age) are given intraperitoneal injections with N3pGlu Aβ antibody (201c) or negative control IgG. Six mice per group receive one 40 mg/kg injection of antibody on day 1 and on day 3. In vivo target engagement is determined on day 6, when mice are sacrificed and brains are collected for histochemical analyses.

The extent of in vivo target engagement is quantified as the percent area positive for the in vivo N3pGlu Aβ antibody engagement normalized to the total plaque area as defined by exogenous 3D6 antibody immunostaining on sister sections (TE Ratio). The TE Ratio is generated by measuring the percent of area bound by the antibody and normalizing the value against the total percent of area of possible target (total deposited Aβ visualized by exogenous immunohistochemistry with a positive control antibody (3D6) on a sister section).

Following procedures essentially as described above, the 201c antibody had a TE Ratio of 2.8%. The 201c antibody demonstrated in vivo target engagement within the hippocampus and to a limited extent in the cortex, whereas the animals injected with control IgG show no plaque-specific staining.

In Vivo Plaque Clearance

Studies are performed with chimera surrogate antibodies with LCVR and HCVR of 201c or 201c H3B fused to murine constant kappa region and IgG2a Fc to evaluate in vivo plaque clearance in aged PDAPP mice. Aged PDAPP mice (21-months of age, n=23 to 25 per group) are injected subcutaneously once a week for 7 weeks with 12.5 mg/kg of chimera 201c antibody, chimera 201c H3B antibody, or control IgG. Control aged PDAPP mice (sacrificed at the onset of the study) are used to evaluate the levels of pre-existing deposition prior to therapeutic treatment.

At the conclusion of the study, final drug levels are measured in plasma, and brains are evaluated by ELISA for levels of $A\beta_{1-42}$. The aged PDAPP mice are at the plaque ceiling as evidenced by a non-significant further accrual of $A\beta_{1-42}$ over the 7-week treatment period with the control IgG. The 201c chimera antibody group and the 201c H3B chimera antibody group show significant reduction in $A\beta_{1-42}$ (26%, p<0.0182 and 26%, p=0.0121, respectively) compared to control. Antibody exposure level was measured at the end of 7-week dosing period, and 201c chimera had a level of 91 µg/mL, and 201c H3B had a level of 56 µg/mL. This study demonstrated that the exemplified chimera N3pGlu Aβ antibody 201c was able to lower plaque ($A\beta_{1-42}$) in vivo.

Lack of Low Affinity Plasma Binding

In vitro studies are performed to investigate potential low-affinity interactions of anti-N3PG antibodies of the present invention (201c and 201cYD) with plasma proteins. Antibody 201c, 201cYD, or 201c H3B is covalently coupled to Sepharose beads and incubated with 10 mls of normal human plasma for 2 hours at 37° C. before performing column chromatography. The bead/plasma mixture was packed into columns and washed. Selectively bound proteins are eluted with glycine (pH 2.5) in different fractions. Each fraction is then analyzed on high-resolution sodium dodecyl sulfate (SDS)-polyacrylamide gel electrophoresis (PAGE) gradient gels (4% to 16%). Silver stain is used to visualize the proteins and bands of interest were excised and analyzed by mass spectrometry. In parallel, multiple control human IgG1 antibodies are analyzed.

Following procedures essentially as described above, visualization of the silver stained gels demonstrated the presence of histidine rich glycoprotein (~64 kDa band), fibrinogen alpha-chain (~60 kDa band), and fibrinogen beta-chain (~50 kDa band) in fraction-5 from the 201c H3B antibody elution as compared to the control IgG1 antibodies. Conversely, the 201c and 201cYD antibodies lacked appreciable low affinity binding to human plasma proteins as compared to the control IgG and the 201c H3B antibody.

Ex Vivo T-Cell Proliferation EpiScreen Assay

An EpiScreen® ex vivo human T-cell assay is used to measure activation (proliferation, cytokine secretion) of human CD4+ T cells in response to an exemplified N3pGlu Aβ antibody of the present invention (201c) or the 201c H3B antibody. EpiScreen® utilizes samples from 50 healthy donors that best represent the number and frequency of HLA-DR and DQ allotypes expressed in the European/North American and world populations. Two positive controls are included in the assay: humanized A33, a clinical benchmark antibody that shows high levels of immunogenicity in the clinic (73%) and routinely induces 20-30% T-cell response in the EpiScreen® assay, and KLH (keyhole limpet hemocyanin), a mitogen-like protein containing neoantigens. A matched buffer negative control is also included in the assay.

The percent of T-cell proliferation is calculated from the average of all positive donor responses observed during the time course (days 5-8). The percent T-cell proliferation was 20% and 94% for the positive controls A33 and KLH, respectively, and was 24% for 201c H3B. However, the percent T-cell proliferation was 10% for 201c. These data demonstrate that the 201c antibody has a low T-cell response rate compared to positive controls and the 201c H3B antibody.

In Silico Immunogenicity Analysis

An EpiMatrix® assay scans protein sequences for potential T-cell epitopes and uses an algorithm to predict immunogenicity. It also considers Tregitope content and the effect on negatively regulating immunogenic response. The amino acid sequences of antibodies 201c, 201cYD, and B12L (antibody B12L comprises a heavy chain given by SEQ ID NO: 23 and a light chain given by SEQ ID NO: 24) were analyzed by EpiMatrix®. The EpiMatrix® predicted scores are shown below in Table 3.

TABLE 3

| | EpiMatrix ® scores. | | |
|---|---|---|---|
| Antibody | EpiMatrix Protein Score | Tregitope-Adjusted EpiMatrix Protein Score | Predicted T-Dependent Ab Response |
| 201c | 39.14 | −35.49 | 0.28% |
| 201cYD | 24.76 | −49.87 | 0.00% |
| B12L | 0.44 | −17.92 | 4.03% |

These data demonstrate that the predicted T cell-dependent antibody response is lower for the N3pGlu Aβ antibodies of the present invention (201c and 201cYD) as compared to the B12L antibody.

Lack of Anti-Drug Antibody (ADA) Recognition

An Affinity Capture Elution (ACE) Bridge assay using biotin and ruthenium labeled 201c or biotin and ruthenium labeled 201cYD is performed in order to assess whether anti-drug antibodies directed against the LY3002813 antibody could bind to 201c or 201cYD.

In this assay format, the ADA bridge between the two labeled antibodies (e.g. biotin and ruthenium labeled 201c). The complex then binds to a plate coated with streptavidin (via the biotin-labeled antibody) and the detection uses Ruthenium to generate signal in a Mesoscale platform. If the ADA does not recognize either the 201c or 201cYD antibody, no signal will be generated. Rabbit anti-human IgG most likely binds preferentially to the Fc, and is used as a positive control to show that labeled 201c or 201cYD could bind antibodies.

The antibodies directed against LY3002813 include antibodies affinity purified from two patient samples from a clinical trial (I5T-MC-AACC NCT01837641) after LY3002813 administration. These patients had developed ADA response for LY3002813 over time as shown by a positive binding signal in ACE bridge.

Following procedures essentially as described above, no signal was observed above background when detecting binding of either 201c or 201cYD to antibodies against LY3002813. These data demonstrate that ADA directed against LY3002813 in humans does not recognize 201c and 201cYD.

Sequences
Antibody 201c, Antibody 201cYD, and Antibody 201c H3B HCDR1
(SEQ ID NO: 1)
AASGFTFSSYPMS Antibody 201c, Antibody 201cYD, and Antibody 201c H3B HCDR2
(SEQ ID NO: 2)
AISGSGGSTYYADSVKG Antibody 201c and Antibody 201cYD HCDR3
(SEQ ID NO: 3)
AREGGSGSYYNGFDY Antibody 201c and Antibody 201c H3B LCDR1
(SEQ ID NO: 4)
RASQSLGNWLA Antibody 201cYD LCDR1
(SEQ ID NO: 5)
RASQSLGNYLA Antibody 201c and Antibody 201c H3B LCDR2
(SEQ ID NO: 6)
YQASTLES Antibody 201cYD LCDR2
(SEQ ID NO: 7)
YDASTLES Antibody 201c, Antibody 201cYD, and Antibody 201c H3B LCDR3
(SEQ ID NO: 8)
QHYKGSFWT Antibody 201c and Antibody 201cYD HCVR
(SEQ ID NO: 9)
EVQLLESGGGLVQPGGSLRLSCAASGFTFSSYPMSWVRQAPGKGLEWVSAISGS
GGSTYYADSVKGRFTISRDNSKNTLYLQMNSLRAEDTAVYYCAREGGSGSYYN
GFDYWGQGTLVTVSS Antibody 201c and Antibody 201c H3B LCVR
(SEQ ID NO: 10)
DIQMTQSPSTLSASVGDRVTITCRASQSLGNWLAWYQQKPGKAPKLLIYQASTLE
SGVPSRFSGSGSGTEFTLTISSLQPDDFATYYCQHYKGSFWTFGQGTKVEIK Antibody 201cYD LCVR
(SEQ ID NO: 11)
DIQMTQSPSTLSASVGDRVTITCRASQSLGNYLAWYQQKPGKAPKLLIYDASTLE
SGVPSRFSGSGSGTEFTLTISSLQPDDFATYYCQHYKGSFWTFGQGTKVEIK Antibody 201c and Antibody 201cYD Heavy Chain
(SEQ ID NO: 12)
EVQLLESGGGLVQPGGSLRLSCAASGFTFSSYPMSWVRQAPGKGLEWVSAISGS
GGSTYYADSVKGRFTISRDNSKNTLYLQMNSLRAEDTAVYYCAREGGSGSYYN
GFDYWGQGTLVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVD
KKVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCSVMHE
ALHNHYTQKSLSLSPG Antibody 201c and Antibody 201c H3B Light Chain
(SEQ ID NO: 13)
DIQMTQSPSTLSASVGDRVTITCRASQSLGNWLAWYQQKPGKAPKLLIYQASTLE
SGVPSRFSGSGSGTEFTLTISSLQPDDFATYYCQHYKGSFWTFGQGTKVEIKRTVA
APSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC Antibody 201cYD Light Chain
(SEQ ID NO: 14)
DIQMTQSPSTLSASVGDRVTITCRASQSLGNYLAWYQQKPGKAPKLLIYDASTLE
SGVPSRFSGSGSGTEFTLTISSLQPDDFATYYCQHYKGSFWTFGQGTKVEIKRTVA
APSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC Exemplified DNA for Expressing Antibody Heavy Chain of SEQ ID NO: 12
(SEQ ID NO: 15)
gaggtgcagctgttggagtctgggggaggcttggtacagcctggggggtccctgagactctcctgtgcagcctctggattcacct
ttagcagctatcctatgagctgggtccgccaggctccagggaaggggctggagtgggtctcagctattagtggtagtggtggtag
cacatactacgcagactccgtgaagggccggttcaccatctccagagacaattccaagaacacgctgtatctgcaaatgaacag
cctgagagccgaggacacggccgtatattactgtgcgagagagggggggctcagggagttattataacggctttgattattgggg -continued

```
ccagggaaccctggtcaccgtctcctcagcctccaccaagggcccatcggtcttcccgctagcaccctcctccaagagcacctc
tgggggcacagcggccctgggctgcctggtcaaggactacttccccgaaccggtgacggtgtcgtggaactcaggcgccctg
accagcggcgtgcacaccttcccggctgtcctacagtcctcaggactctactccctcagcagcgtggtgaccgtgccctccagc
agcttgggcacccagacctacatctgcaacgtgaatcacaagcccagcaacaccaaggtggacaagaaagttgagcccaaatc
ttgtgacaaaactcacacatgcccaccgtgcccagcacctgaactcctggggggaccgtcagtcttcctcttccccccaaaaccc
aaggacaccctcatgatctcccggacccctgaggtcacatgcgtggtggtggacgtgagccacgaagaccctgaggtcaagtt
caactggtacgtggacggcgtggaggtgcataatgccaagacaaagccgcgggaggagcagtacaacagcacgtaccgtgt
ggtcagcgtcctcaccgtcctgcaccaggactggctgaatggcaaggagtacaagtgcaaggtctccaacaaagccctcccag
cccccatcgagaaaaccatctccaaagccaaagggcagccccgagaaccacaggtgtacaccctgcccccatcccgggacg
agctgaccaagaaccaggtcagcctgacctgcctggtcaaaggcttctatcccagcgacatcgccgtggagtgggagagcaat
gggcagccggagaacaactacaagaccacgcccccgtgctggactccgacggctccttcttcctctatagcaagctcaccgtg
gacaagagcaggtggcagcaggggaacgtcttctcatgctccgtgatgcatgaggctctgcacaaccactacacgcagaagag
cctctccctgtctccgggt
```

Exemplified DNA for Expressing Antibody Light Chain of SEQ ID NO: 13

(SEQ ID NO: 16)

```
gacatccagatgacccagtctccttccaccctgtctgcatctgtaggagacagagtcaccatcacttgccgggccagtcagagtct
tggtaactggttggcctggtatcagcagaaaccagggaaagcccctaaactcctgatctatcaggcgtctactttagaatctgggg
tcccatcaagattcagcggcagtggatctgggacagagttcactctcaccatcagcagcctgcagcctgatgattttgcaacttatt
actgccaacattataaaggttcttttggacgttcggccaagggaccaaggtggaaatcaaacgaccgtggctgcaccatctgtc
ttcatcttcccgccatctgatgagcagttgaaatctggaactgcctctgttgtgtgcctgctgaataacttctatcccagagaggcca
aagtacagtggaaggtggataacgcccctccaatcgggtaactcccaggagagtgtcacagagcaggacagcaaggacagca
cctacagcctcagcagcaccctgacgctgagcaaagcagactacgagaaacacaaagtctacgcctgcgaagtcacccatca
gggcctgagctcgcccgtcacaaagagcttcaacaggggagagtgc
```

Exemplified DNA for Expressing Antibody Light Chain of SEQ ID NO: 14

(SEQ ID NO: 17)

```
gacatccagatgacccagtctccttccaccctgtctgcatctgtaggagacagagtcaccatcacttgccgggccagtcagagtct
tggtaactatttggcctggtatcagcagaaaccagggaaagcccctaaactcctgatctatgatgcgtctactttagaatctgggt
cccatcaagattcagcggcagtggatctgggacagagttcactctcaccatcagcagcctgcagcctgatgattttgcaacttatta
ctgccaacattataaaggttcttttggacgttcggccaagggaccaaggtggaaatcaaacgaccgtgtctgcaccatctgtct
tcatcttcccgccatctgatgagcagttgaaatctggaactgcctctgttgtgtgcctgctgaataacttctatcccagagaggccaa
agtacagtggaaggtggataacgcccctccaatcgggtaactcccaggagagtgtcacagagcaggacagcaaggacagcac
ctacagcctcagcagcaccctgacgctgagcaaagcagactacgagaaacacaaagtctacgcctgcgaagtcacccatcag
ggcctgagctcgcccgtcacaaagagcttcaacaggggagagtgc
```

Antibody 201c H3B HCDR3

(SEQ ID NO: 18)

AREGGSGSYFNGFDY

Antibody 201c H3B HCVR (SEQ ID NO: 19)

EVQLLESGGGLVQPGGSLRLSCAASGFTFSSYPMSWVRQAPGKGLEWVSAISGS
GGSTYYADSVKGRFTISRDNSKNTLYLQMNSLRAEDTAVYYCAREGGSGSYFNG
FDYWGQGTLVTVSS

Antibody 201c H3B Heavy Chain (SEQ ID NO: 20)

EVQLLESGGGLVQPGGSLRLSCAASGFTFSSYPMSWVRQAPGKGLEWVSAISGS
GGSTYYADSVKGRFTISRDNSKNTLYLQMNSLRAEDTAVYYCAREGGSGSYFNG
FDYWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSVMHE
ALHNHYTQKSLSLSPG

Exemplified DNA for Expressing Antibody Heavy Chain of SEQ ID NO: 20

(SEQ ID NO: 21)

```
gaggtgcagctgttggagtctgggggaggcttggtacagcctggggggtccctgagactctcctgtgcagcctctggattcacct
ttagcagctatcctatgagctggtccgccaggctccagggaaggggctggagtgggtctcagctattagtggtagtggtggtag
cacatactacgcagactccgtgaagggccggttcaccatctccagagacaattccaagaacacgctgtatctgcaaatgaacag
cctgagagccgaggacaccgccgtatattactgtgcgagagaggggggctcagggagttatttaacggctttgattattgggc
cagggaaccctggtcaccgtctcctcagcctccaccaagggcccatcggtcttcccgctagcaccctcctccaagagcacctct
gggggcacagcggccctgggctgcctggtcaaggactacttccccgaaccggtgacggtgtcgtggaactcaggcgccctga
ccagcggcgtgcacaccttcccggctgtcctacagtcctcaggactctactccctcagcagcgtggtgaccgtgccctccagca
gcttgggcacccagacctacatctgcaacgtgaatcacaagcccagcaacaccaaggtggacaagaaagttgagcccaaatct
tgtgacaaaactcacacatgcccaccgtgcccagcacctgaactcctggggggaccgtcagtcttcctcttccccccaaaaccca
aggacaccctcatgatctcccggacccctgaggtcacatgcgtggtggtggacgtgagccacgaagaccctgaggtcaagttc
aactggtacgtggacggcgtggaggtgcataatgccaagacaaagccgcgggaggagcagtacaacagcacgtaccgtgtg
gtcagcgtcctcaccgtcctgcaccaggactggctgaatggcaaggagtacaagtgcaaggtctccaacaaagccctcccagc
ccccatcgagaaaaccatctccaaagccaaagggcagccccgagaaccacaggtgtacaccctgcccccatcccgggagc
gctgaccaagaaccaggtcagcctgacctgcctggtcaaaggcttctatcccagcgacatcgccgtggagtgggagagcaatg
ggcagccggagaacaactacaagaccacgcccccgtgctggactccgacggctccttcttcctctatagcaagctcaccgtgg
acaagagcaggtggcagcaggggaacgtcttctcatgctccgtgatgcatgaggctctgcacaaccactacacgcagaagagc
ctctccctgtctccgggt
```

-continued

N3pGlu Aβ
(SEQ ID NO: 22)

[pE]FRHDSGYEVHHQKLVFFAEDVGSNKGAIIGLMVGGVVIA

Antibody B12L Heavy Chain
(SEQ ID NO: 23)

QVQLVQSGAEVKKPGSSVKVSCKASGYDFTRYYINWVRQAPGQGLEWMGWINP
GSGNTKYNEKFKGRVTITADESTSTAYMELSSLRSEDTAVYYCAREGITVYWGQ
GTTVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKS
CDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKA
LPAPIEKTISKAKGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHY
TQKSLSLSPG

Antibody B12L Light Chain
(SEQ ID NO: 24)

DIVMTQTPLSLSVTPGQPASISCKSSQSLLYSRGKTYLNWLLQKPGQSPQLLIYAV
SKLDSGVPDRFSGSGSGTDFTLKISRVEAEDVGVYYCVQGTHYPFTFGQGTKLEI
KRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC

---

We claim:

1. A DNA molecule comprising a polynucleotide that encodes an antibody heavy chain comprising SEQ ID NO:12.

2. The DNA molecule of claim 1, wherein the polynucleotide comprises SEQ ID NO: 15.

3. A DNA molecule comprising a polynucleotide that encodes an antibody light chain comprising SEQ ID NO:13.

4. The DNA molecule of claim 3, wherein the polynucleotide comprises SEQ ID NO: 16.

5. A DNA molecule comprising a polynucleotide sequence that encodes an antibody heavy chain comprising SEQ ID NO: 12 and a polynucleotide sequence that encodes an antibody light chain comprising SEQ ID NO: 13.

6. The DNA molecule of claim 5, wherein the polynucleotide sequence that encodes the antibody heavy chain is SEQ ID NO:15, and the polynucleotide sequence that encodes the antibody light chain is SEQ ID NO:16.

7. A mammalian cell transformed with a DNA molecule comprising: a polynucleotide that encodes an antibody heavy chain comprising SEQ ID NO: 12 and/or a polynucleotide that encodes an antibody light chain comprising SEQ ID NO: 13.

8. The mammalian cell of claim 7 transformed with the DNA molecule comprising: a polynucleotide that encodes the antibody heavy chain comprising SEQ ID NO: 12 and a polynucleotide that encodes the antibody light chain comprising SEQ ID NO: 13.

9. A process for producing an antibody comprising two heavy chains and two light chains, wherein each heavy chain comprises SEQ ID NO: 12, and each light chain comprises SEQ ID NO: 13, and wherein the process comprises: a) expressing the antibody under suitable conditions in a mammalian cell, and b) recovering the expressed antibody.

* * * * *

UNITED STATES PATENT AND TRADEMARK OFFICE
CERTIFICATE OF CORRECTION

PATENT NO. : 11,078,261 B2  
APPLICATION NO. : 16/843503  
DATED : August 3, 2021  
INVENTOR(S) : Ronald Bradley Demattos, Jirong Lu and Ying Tang It is certified that error appears in the above-identified patent and that said Letters Patent is hereby corrected as shown below:

On the Title Page

In the OTHER PUBLICATIONS listing, please correct the following entries:

Column 2, Line 36: "Blomarkers" should read --Biomarkers--

Column 2, Line 39: "Immunotiierapy" should read --Immunotherapy--

Signed and Sealed this  
Seventh Day of December, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 24

<210> SEQ ID NO 1
<211> LENGTH: 13
<212> TYPE: PRT
<213> ORGANISM: Artificial Sequence
<220> FEATURE:
<223> OTHER INFORMATION: Synthetic construct

<400> SEQUENCE: 1

Ala Ala Ser Gly Phe Thr Phe Ser Ser Tyr Pro Met Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic construct

<400> SEQUENCE: 2

Ala Ile Ser Gly Ser Gly Gly Ser Thr Tyr Tyr Ala Asp Ser Val Lys
1               5                   10                  15

Gly

<210> SEQ ID NO 3
<211> LENGTH: 15
<212> TYPE: PRT
<213> ORGANISM: Artificial Sequence
<220> FEATURE:
<223> OTHER INFORMATION: Synthetic Construct

<400> SEQUENCE: 3

Ala Arg Glu Gly Gly Ser Gly Ser Tyr Tyr Asn Gly Phe Asp Tyr
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

```
Arg Ala Ser Gln Ser Leu Gly Asn Trp Leu Ala
1               5                   10
```

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

```
Arg Ala Ser Gln Ser Leu Gly Asn Tyr Leu Ala
1               5                   10
```

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

```
Tyr Gln Ala Ser Thr Leu Glu Ser
1               5
```

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

```
Tyr Asp Ala Ser Thr Leu Glu Ser
1               5
```

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

```
Gln His Tyr Lys Gly Ser Phe Trp Thr
1               5
```

<210> SEQ ID NO 9
<211> LENGTH: 122
<212> TYPE: PRT
<213> ORGANISM: Artificial Sequence
<220> FEATURE:
<223> OTHER INFORMATION: Synthetic Construct

<400> SEQUENCE: 9

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Arg Glu Gly Gly Ser Gly Ser Tyr Tyr Asn Gly Phe Asp Tyr Trp
            100                 105                 110

Gly Gln Gly Thr Leu Val Thr Val Ser Ser
            115                 120
```

<210> SEQ ID NO 10
<211> LENGTH: 107
<212> TYPE: PRT
<213> ORGANISM: Artificial Sequence
<220> FEATURE:
<223> OTHER INFORMATION: Synthetic Construct

<400> SEQUENCE: 10

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Leu Gly Asn Trp
            20                  25                  30

Leu Ala Trp Tyr Gln Gln Lys Pro Gly Lys Ala Pro Lys Leu Leu Ile
            35                  40                  45

Tyr Gln Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Lys Gly Ser Phe Trp
                85                  90                  95

Thr Phe Gly Gln Gly Thr Lys Val Glu Ile Lys
            100                 105
```

<210> SEQ ID NO 11
<211> LENGTH: 107
<212> TYPE: PRT
<213> ORGANISM: Artificial Sequence
<220> FEATURE:
<223> OTHER INFORMATION: Synthetic Construct

<400> SEQUENCE: 11

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Leu Gly Asn Tyr
            20                  25                  30

Leu Ala Trp Tyr Gln Gln Lys Pro Gly Lys Ala Pro Lys Leu Leu Ile
            35                  40                  45

Tyr Asp Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Lys Gly Ser Phe Trp
                85                  90                  95

Thr Phe Gly Gln Gly Thr Lys Val Glu Ile Lys
            100                 105
```

<210> SEQ ID NO 12
<211> LENGTH: 451
<212> TYPE: PRT
<213> ORGANISM: Artificial Sequence
<220> FEATURE:
<223> OTHER INFORMATION: Synthetic Construct

<400> SEQUENCE: 12

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Ser Gly Ser Tyr Tyr Asn Gly Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
```

```
                        405                 410                 415
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 13
<211> LENGTH: 214
<212> TYPE: PRT
<213> ORGANISM: Artificial Sequence
<220> FEATURE:
<223> OTHER INFORMATION: Synthetic Construct

<400> SEQUENCE: 13

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Leu Gly Asn Trp
            20                  25                  30

Leu Ala Trp Tyr Gln Gln Lys Pro Gly Lys Ala Pro Lys Leu Leu Ile
        35                  40                  45

Tyr Gln Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Lys Gly Ser Phe Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 214
<212> TYPE: PRT
<213> ORGANISM: Artificial Sequence
<220> FEATURE:
<223> OTHER INFORMATION: Synthetic Construct

<400> SEQUENCE: 14

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Leu Gly Asn Tyr
            20                  25                  30
```

| Leu | Ala | Trp | Tyr | Gln | Gln | Lys | Pro | Gly | Lys | Ala | Pro | Lys | Leu | Leu | Ile |
|---|---|---|---|---|---|---|---|---|---|---|---|---|---|---|---|
| | | | 35 | | | | 40 | | | | 45 | | | | |

| Tyr | Asp | Ala | Ser | Thr | Leu | Glu | Ser | Gly | Val | Pro | Ser | Arg | Phe | Ser | Gly |
|---|---|---|---|---|---|---|---|---|---|---|---|---|---|---|---|
| 50 | | | | | 55 | | | | | 60 | | | | | |

| Ser | Gly | Ser | Gly | Thr | Glu | Phe | Thr | Leu | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Asp | Asp | Phe | Ala | Thr | Tyr | Tyr | Cys | Gln | His | Tyr | Lys | Gly | Ser | Phe | Trp |
|---|---|---|---|---|---|---|---|---|---|---|---|---|---|---|---|
| | | | | 85 | | | | 90 | | | | | 95 | | |

| Thr | Phe | Gly | Gln | Gly | Thr | Lys | Val | Glu | Ile | Lys | Arg | Thr | Val | Ala | Ala |
|---|---|---|---|---|---|---|---|---|---|---|---|---|---|---|---|
| | | | 100 | | | | | 105 | | | | | 110 | | |

| Pro | Ser | Val | Phe | Ile | Phe | Pro | Pro | Ser | Asp | Glu | Gln | Leu | Lys | Ser | Gly |
|---|---|---|---|---|---|---|---|---|---|---|---|---|---|---|---|
| | 115 | | | | | 120 | | | | | 125 | | | | |

| Thr | Ala | Ser | Val | Val | Cys | Leu | Leu | Asn | Asn | Phe | Tyr | Pro | Arg | Glu | Ala |
|---|---|---|---|---|---|---|---|---|---|---|---|---|---|---|---|
| | 130 | | | | | 135 | | | | | 140 | | | | |

| Lys | Val | Gln | Trp | Lys | Val | Asp | Asn | Ala | Leu | Gln | Ser | Gly | Asn | Ser | Gln |
|---|---|---|---|---|---|---|---|---|---|---|---|---|---|---|---|
| 145 | | | | | 150 | | | | | 155 | | | | | 160 |

| Glu | Ser | Val | Thr | Glu | Gln | Asp | Ser | Lys | Asp | Ser | Thr | Tyr | Ser | Leu | Ser |
|---|---|---|---|---|---|---|---|---|---|---|---|---|---|---|---|
| | | | 165 | | | | | 170 | | | | | 175 | | |

| Ser | Thr | Leu | Thr | Leu | Ser | Lys | Ala | Asp | Tyr | Glu | Lys | His | Lys | Val | Tyr |
|---|---|---|---|---|---|---|---|---|---|---|---|---|---|---|---|
| | | | 180 | | | | | 185 | | | | | 190 | | |

| Ala | Cys | Glu | Val | Thr | His | Gln | Gly | Leu | Ser | Ser | Pro | Val | Thr | Lys | Ser |
|---|---|---|---|---|---|---|---|---|---|---|---|---|---|---|---|
| | | 195 | | | | | 200 | | | | | 205 | | | |

| Phe | Asn | Arg | Gly | Glu | Cys |
|---|---|---|---|---|---|
| | 210 | | | | |

<210> SEQ ID NO 15
<211> LENGTH: 1353
<212> TYPE: DNA
<213> ORGANISM: Artificial Sequence
<220> FEATURE:
<223> OTHER INFORMATION: Synthetic Construct

<400> SEQUENCE: 15

```
gaggtgcagc tgttggagtc tgggggaggc ttggtacagc ctggggggtc cctgagactc      60
tcctgtgcag cctctggatt cacctttagc agctatccta tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gagagagggg     300
ggctcaggga gttattataa cggctttgat tattgggggcc agggaaccct ggtcaccgtc     360
tcctcagcct ccaccaaggg cccatcggtc ttccccgcta cccctcctc caagagcacc     420
tctgggggca gcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagaaagtt     660
gagcccaaat cttgtgacaa aactcacaca tgcccaccgt gcccagcacc tgaactcctg     720
gggggaccgt cagtcttcct cttccccca aaacccaagg acaccctcat gatctcccgg     780
acccctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgtgt ggtcagcgtc ctcaccgtcc tgcaccagga ctggctgaat     960
ggcaaggagt acaagtgcaa ggtctccaac aaagccctcc cagcccccat cgagaaaacc    1020
```

```
atctccaaag ccaaagggca gccccgagaa ccacaggtgt acaccctgcc cccatcccgg   1080
gacgagctga ccaagaacca ggtcagcctg acctgcctgg tcaaaggctt ctatcccagc   1140
gacatcgccg tggagtggga gagcaatggg cagccggaga caactacaa gaccacgccc    1200 cccgtgctgg actccgacgg ctccttcttc ctctatagca agctcaccgt ggacaagagc   1260
aggtggcagc aggggaacgt cttctcatgc tccgtgatgc atgaggctct gcacaaccac   1320
tacacgcaga gagcctctc cctgtctccg ggt                                 1353

<210> SEQ ID NO 16
<211> LENGTH: 642
<212> TYPE: DNA
<213> ORGANISM: Artificial Sequence
<220> FEATURE:
<223> OTHER INFORMATION: Synthetic Construct

<400> SEQUENCE: 16
gacatccaga tgacccagtc tccttccacc ctgtctgcat ctgtaggaga cagagtcacc     60
atcacttgcc gggccagtca gagtcttggt aactggttgg cctggtatca gcagaaacca   120
gggaaagccc ctaaactcct gatctatcag gcgtctactt tagaatctgg ggtcccatca   180
agattcagcg gcagtggatc tgggacagag ttcactctca ccatcagcag cctgcagcct   240
gatgattttg caacttatta ctgccaacat tataaaggtt cttttggac gttcggccaa    300 gggaccaagg tggaaatcaa acggaccgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gc                      642

<210> SEQ ID NO 17
<211> LENGTH: 642
<212> TYPE: DNA
<213> ORGANISM: Artificial Sequence
<220> FEATURE:
<223> OTHER INFORMATION: Synthetic Construct

<400> SEQUENCE: 17
gacatccaga tgacccagtc tccttccacc ctgtctgcat ctgtaggaga cagagtcacc     60
atcacttgcc gggccagtca gagtcttggt aactatttgg cctggtatca gcagaaacca   120
gggaaagccc ctaaactcct gatctatgat gcgtctactt tagaatctgg ggtcccatca   180
agattcagcg gcagtggatc tgggacagag ttcactctca ccatcagcag cctgcagcct   240
gatgattttg caacttatta ctgccaacat tataaaggtt cttttggac gttcggccaa    300 gggaccaagg tggaaatcaa acggaccgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gc                      642

<210> SEQ ID NO 18
```

```
<211> LENGTH: 15
<212> TYPE: PRT
<213> ORGANISM: Artificial Sequence
<220> FEATURE:
<223> OTHER INFORMATION: Synthetic Construct

<400> SEQUENCE: 18

Ala Arg Glu Gly Gly Ser Gly Ser Tyr Phe Asn Gly Phe Asp Tyr
1               5                   10                  15

<210> SEQ ID NO 19
<211> LENGTH: 122
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Ser Gly Ser Tyr Phe Asn Gly Phe Asp Tyr Trp
            100                 105                 110

Gly Gln Gly Thr Leu Val Thr Val Ser Ser
        115                 120

<210> SEQ ID NO 20
<211> LENGTH: 451
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Ser Gly Ser Tyr Phe Asn Gly Phe Asp Tyr Trp
            100                 105                 110

Gly Gln Gly Thr Leu Val Thr Val Ser Ser Ala Ser Thr Lys Gly Pro
        115                 120                 125
```

```
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly
    450

<210> SEQ ID NO 21
<211> LENGTH: 1353
<212> TYPE: DNA
<213> ORGANISM: Artificial Sequence
<220> FEATURE:
<223> OTHER INFORMATION: Synthetic Construct

<400> SEQUENCE: 21
gaggtgcagc tgttggagtc tgggggaggc ttggtacagc ctggggggtc cctgagactc      60
tcctgtgcag cctctggatt cacctttagc agctatccta tgagctgggt ccgccaggct     120
ccagggaagg ggctggagtg ggtctcagct attagtggta gtggtggtag cacatactac     180
```

```
gcagactccg tgaagggccg gttcaccatc tccagagaca attccaagaa cacgctgtat    240
ctgcaaatga acagcctgag agccgaggac acggccgtat attactgtgc gagagagggg    300
ggctcaggga gttattttaa cggctttgat tattggggcc agggaaccct ggtcaccgtc    360
tcctcagcct ccaccaaggg cccatcggtc ttccccgcta gcacctcctc caagagcacc    420 tctggggggca gcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagaaagtt    660
gagcccaaat cttgtgacaa aactcacaca tgcccaccgt gcccagcacc tgaactcctg    720
gggggaccgt cagtcttcct cttcccccca aaacccaagg acaccctcat gatctcccgg    780
acccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagcccccat cgagaaaacc   1020
atctccaaag ccaaagggca gccccgagaa ccacaggtgt acaccctgcc cccatcccgg   1080
gacgagctga ccaagaacca ggtcagcctg acctgcctgg tcaaaggctt ctatcccagc   1140
gacatcgccg tggagtggga gagcaatggg cagccggaga caactacaa gaccacgccc   1200 cccgtgctgg actccgacgg ctccttcttc ctctatagca agctcaccgt ggacaagagc   1260
aggtggcagc aggggaacgt cttctcatgc tccgtgatgc atgaggctct gcacaaccac   1320
tacacgcaga agagcctctc cctgtctccg ggt                                1353
```

<210> SEQ ID NO 22
<211> LENGTH: 40
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 = pyroglutamic acid

<400> SEQUENCE: 22

Xaa Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40

<210> SEQ ID NO 23
<211> LENGTH: 444
<212> TYPE: PRT
<213> ORGANISM: Artificial Sequence
<220> FEATURE:
<223> OTHER INFORMATION: Synthetic

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asp Phe Thr Arg Tyr
            20                  25                  30

```
Tyr Ile Asn Trp Val Arg Gln Ala Pro Gly Gln Gly Leu Glu Trp Met
         35                  40                  45
Gly Trp Ile Asn Pro Gly Ser Gly Asn Thr Lys Tyr Asn Glu Lys Phe
 50                  55                  60
Lys Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Glu Gly Ile Thr Val Tyr Trp Gly Gln Gly Thr Thr Val Thr
                100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
    195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
    275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
    355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly
    435                 440
```

```
<210> SEQ ID NO 24
<211> LENGTH: 219
<212> TYPE: PRT
<213> ORGANISM: Artificial Sequence
<220> FEATURE:
<223> OTHER INFORMATION: Synthetic

<400> SEQUENCE: 24

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Arg Gly Lys Thr Tyr Leu Asn Trp Leu Leu Gln Lys Pro Gly Gln Ser
        35                  40                  45

Pro Gln Leu Leu Ile Tyr Ala Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Tyr Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```